United States Patent
Cadwell et al.

(10) Patent No.: US 9,683,207 B2
(45) Date of Patent: Jun. 20, 2017

(54) METHOD FOR GROWING CELLS IN HOLLOW FIBERS

(71) Applicants: John J. S. Cadwell, New Market, MD (US); Kevin Barnes, Westminster, MD (US)

(72) Inventors: John J. S. Cadwell, New Market, MD (US); Kevin Barnes, Westminster, MD (US)

(73) Assignee: FIBERCELL PRODUCTION SOLUTIONS LLC, Wilmington, DE (US)

( * ) Notice: Subject to any disclaimer, the term of this patent is extended or adjusted under 35 U.S.C. 154(b) by 0 days.

(21) Appl. No.: 13/874,864

(22) Filed: May 1, 2013

(65) Prior Publication Data
US 2013/0295662 A1 Nov. 7, 2013

Related U.S. Application Data

(60) Provisional application No. 61/641,194, filed on May 1, 2012.

(51) Int. Cl.
*C12M 1/00* (2006.01)
*C12M 1/12* (2006.01)

(52) U.S. Cl.
CPC ............ *C12M 21/00* (2013.01); *C12M 25/10* (2013.01)

(58) Field of Classification Search
CPC ....... C12M 27/16; C12M 21/00; C12M 25/10
USPC ...................................................... 435/297.4
See application file for complete search history.

(56) References Cited

U.S. PATENT DOCUMENTS

| | | | |
|---|---|---|---|
| 4,391,912 A | 7/1983 | Yoshida et al. | |
| 5,622,857 A | 4/1997 | Goffe | |
| 6,566,126 B2 * | 5/2003 | Cadwell | 435/297.4 |
| 6,680,166 B1 | 1/2004 | Mullon et al. | |
| 6,933,144 B2 | 8/2005 | Cadwell | |
| 6,979,308 B1 | 12/2005 | MacDonald et al. | |
| 2005/0186669 A1 * | 8/2005 | Ho et al. | 435/287.1 |
| 2006/0014274 A1 * | 1/2006 | Klaus | C12M 29/16 435/297.4 |

(Continued)

FOREIGN PATENT DOCUMENTS

WO   WO2008136371   * 11/2008

OTHER PUBLICATIONS

W.G. Whitford and J.J.S. Cadwell, Interest in Hollow-Fiber Perfusion Bioreactors Is Growing, BioProcess International, Oct. 2009, pp. 54-63, US.

*Primary Examiner* — Gautam Prakash
(74) *Attorney, Agent, or Firm* — Marsh IP Law

(57) ABSTRACT

A system and method for culturing cells is provided that includes an extra-capillary space between at least one permeable hollow fiber and an enclosed chamber. Cells are placed in the extra-capillary space to grow. One or more reservoirs containing cell-culture media and/or an oxygen-containing gas are provided in communication with the at least one fiber. The system is configured to generate alternating flows of both the cell-culture media and the gas through a lumen of the hollow fiber(s), thereby passing both nutrients and gas through the walls of the fiber(s) to the cells in the extra-capillary space to provide a suitable environment for growth and/or proliferation of the cells. Flows of liquid and gas through the hollow fiber(s) can be produced by gravity and/or various pumping configurations.

13 Claims, 9 Drawing Sheets

(56) References Cited

U.S. PATENT DOCUMENTS

| | | | |
|---|---|---|---|
| 2006/0019391 A1* | 1/2006 | Marx | C12M 29/16 435/297.4 |
| 2007/0037277 A1* | 2/2007 | Shuler et al. | 435/297.4 |
| 2009/0215022 A1* | 8/2009 | Page et al. | 435/286.5 |
| 2010/0159524 A1* | 6/2010 | Smith | C12M 29/16 435/383 |
| 2011/0212493 A1 | 9/2011 | Hirschel et al. | |

* cited by examiner

PRIOR ART

METHOD FOR GROWING CELLS IN HOLLOW FIBERS

CROSS-REFERENCE TO RELATED APPLICATION(S)

This application claims priority to U.S. Provisional Application Ser. No. 61/641,194, filed on May 1, 2012, which is incorporated by reference herein in its entirety.

FIELD OF THE DISCLOSURE

The invention described herein relates to an apparatus and a method for growing suspension and adherent cells in vitro, and more specifically, such apparatus and method that includes hollow permeable fibers that can provide transfer of both liquid-based nutrients and gas to and from cells growing outside of the fibers.

BACKGROUND INFORMATION

Growing living cells in vitro can be performed for a variety of purposes, including the production of cell derivatives and secreted products, the preparation of viral vaccines, expansion and harvesting of the cells themselves, and the recovery of valuable cell by-products. There are a variety of methods used for cell culture at the production level. These can be as simple as banks of roller bottles, disposable bags on a rocking platform, to large stirred vessels having a volume of 10,000 liters or more.

These systems suffer from certain shortcomings. For example, cells bound to a non-porous surface must be split prior to the cells reaching confluence. Adherent cells need to be adapted to suspension culture for production in large tanks. The larger the volume of the reactor, the greater the potential for local variability of cell culture conditions within the system. Also, the volume of cell culture product to be processed can be quite large and the concentration of the desired product can be quite low.

Among the devices that have been developed for growing cells in vitro, the shell-and-tube type arrangement has become fairly common, particularly for growing suspension and adherent cells. Such devices, which can also be referred to as hollow-fiber bioreactors, use permeable tube-shaped hollow fibers (e.g., capillaries), contained within an outer shell, which may be configured so that fluid in a space external to the hollow fibers (an extra-capillary space) is segregated from lumens of the hollow fibers and fluid passing therethrough. Additionally, such devices typically include two manifold end chambers within the outer shell located at opposite ends of the device. Each end of the lumen of a hollow fiber connects to a different end chamber. The end chambers and the fiber lumens are separated from the extra-capillary space by the permeable membranes of the hollow fibers. Transport of aqueous and/or gaseous substances between the fiber lumens and the extra-capillary space can be controlled, to a certain extent, by the molecular weight cutoff, or pore size, of the membranes of the hollow fibers.

Typically, cells in a hollow-fiber bioreactor are grown in the extra-capillary space while a nutrient medium is passed through the hollow fibers. The permeable nature of the hollow fibers allows nutrients and cell waste products and/or by-products to pass through the walls of the hollow fibers while blocking cells from doing the same. For example, U.S. Pat. No. 4,391,912 to Yoshida et al. describes a range of pore diameters to support the transfer of the nutrient medium from the intra-capillary space (e.g., within the lumen of a fiber) to the extra-capillary space, while blocking the entrance of cells into the intra-capillary space.

Shell-and-tube type bioreactors provide several advantages. For adherent cells, the use of several hollow fibers can provide a large amount of surface area upon which the cells can grow within a relatively small reactor volume. For both suspension and adherent cells, this large surface area density can facilitate localized distribution of nutrient media to the growing cells and collection of cell waste products. Hollow-fiber bioreactors thus may enable the growth of cells at much higher densities than is possible with many other cell culture devices. For example, they can support cell densities greater than $10^8$ cells per milliliter, whereas other cell culture devices are typically limited to densities around $10^6$ cells per milliliter. This high cell density facilitates the adaptation of the cells to a simplified serum free medium.

U.S. Pat. No. 6,933,144 of Cadwell describes a hollow-fiber bioreactor that includes a hollow fiber cartridge provided between two deformable bags, where providing nutrients to cells in the extra-capillary volume can be achieved through bi-directional flow of liquid medium between the two bags as they are raised and lowered. The force of gravity impels medium flow through the lumens of the capillaries. Very high flow rates can be achieved through this system and method, which is shown in FIGS. 1-3 and described below.

FIG. 1 shows a cross sectional side view of a prior-art hollow-fiber bioreactor. In this bioreactor, a media reservoir 102 holds cell-culture media 104 and is configured to be rocked or rotated about a horizontal axis of rotation 106 that extends into the drawing sheet of FIG. 1. An enclosed chamber 108 is disposed within the media reservoir 102, wherein an extra-chamber space 110 is defined between the media reservoir 102 and the enclosed chamber 108. A plurality of hollow fibers 112 pass through the enclosed chamber 108 and are secured at each end by a first potting structure 114 and a second potting structure 116. An extra-capillary space 118 is defined between an interior of the enclosed chamber 108 and the exterior surfaces of the hollow fibers 112. For example, the fibers 112 are potted at the ends of the chamber 108 such that any liquid media 104 entering the end of the chamber 108 passes through the fiber lumens and out the other end of the chamber 108, such that no media 104 directly enters the extra-capillary space 118 as it flows through the reactor, but remains separated from the extra-capillary space 118 by the walls of the fibers 112. The hollow fibers 112 are oriented substantially parallel to a longitudinal axis 120, which can be substantially perpendicular to the horizontal axis of rotation 106.

The media reservoir 102 can include an opening 122 for accessing the extra-chamber space 110, e.g., to allow fresh cell-culture media to be supplied to the media reservoir 102, to allow stale cell-culture media to be removed from the media reservoir 102, and/or to facilitate removal of cell waste products from the media reservoir 102. A lid 124 can be provided to seal the opening 122. The media reservoir 102 can also include one or more openings 126 for accessing the extra-capillary space 118. For example, the opening 126 includes a port 128 passing through the extra-chamber space 110 to provide access to the extra-capillary space 118. The opening 126 allows developing cells to be placed into extra-capillary space 118, mature cells to be removed from the extra-capillary space 118, secreted products to be harvested from the extra-capillary space 118, and/or administration of reagents, drugs, and/or DNA or RNA vectors to the cells.

The media reservoir 102 can also include a gas-permeable membrane 130 permitting gas exchange between an environment exterior to the media reservoir 102 and the extra-chamber space 110. The membrane 130 permits the exchange of the waste gases from the extra-chamber space 110 with fresh gases from the environment exterior to the media reservoir 102. Transverse members 134 provide support to the media reservoir 102 along a face that includes membrane 130. A dam 136 is disposed in the media reservoir 102 to impede flow of cell-culture media 104 within the extra-chamber space 110 when the media reservoir 102 is rocked or rotated about the horizontal axis of rotation 106. The dam 136 also serves to encourage flow of cell-culture media 104 through the hollow fibers 112. If the enclosed chamber 108 spans the width of the media reservoir 102 along the horizontal axis of rotation 106, the enclosed chamber 108 and dam 136 can be integrated.

FIG. 2 is a cutaway end view showing a partial cross section of the hollow-fiber bioreactor shown in FIG. 1 taken along section A-A'. In FIG. 2, each hollow fiber 112 has a central lumen 202 that is open at each end to the extra-chamber space 110, such that cell-culture media 104 can pass through the lumens 202 of hollow fibers 112, e.g., to facilitate passage of nutrients through the walls of hollow fibers 112 to nourish the cells in the extra-capillary space 118.

FIG. 3 illustrates how a rocking or rotating motion causes the flow of cell-culture media in the hollow-fiber bioreactor shown in FIG. 1. By impeding the flow of cell-culture media 104 in the extra-chamber space 110, the dam 136 simultaneously increases the static head pressure of a raised portion 302 of cell-culture media 104 and decreases the static head pressure of a lowered portion 304 of cell-culture media 104 that would otherwise exist in the absence of dam 134. Thus, by increasing the differential pressure across the hollow fibers 112, the dam 136 serves to encourage flow of cell-culture media 104 through the hollow fibers 112 when the reactor is tilted around the axis 106.

The length of time the cells can be cultured in a conventional hollow-fiber bioreactor may be extended to many months, such that scale up of production can be achieved by longer culture times rather than by using different equipment. However, it is generally recognized that the delivery of oxygen to cells growing in these systems can present a limitation to the size of hollow fiber bioreactors. This is primarily due to the low solubility of gases such as oxygen and carbon dioxide in aqueous solutions at the temperatures required for cell culture, and limitations of flow rate generated by such bioreactor systems. This physicochemical phenomenon has an impediment to the creation and adoption of larger scale hollow fiber cell culture systems.

Insufficient oxygenation represents a primary shortcoming of conventional hollow fiber bioreactor systems, and is the primary reason that the technology is underutilized and cannot be used at a scale practicable for larger scale biomanufacturing despite its many advantages. There are examples in the prior art that attempt to address these issues, without particular success. For example, gas exchange can be accomplished by passing the medium through a device that passively diffuses gas into the medium prior to entering the hollow fiber cartridge, where such gases may then pass (in a limited fashion) through the walls of the fibers and into the extra-capillary volume where the cells are located. An example of this approach is described in US Patent Publication No. 2010/0159524 of Smith et. al. A bioreactor system that uses two fiber types within the cartridge, one to deliver a nutrient medium and one to deliver gas, is described in U.S. Pat. No. 5,622,857 of Goffe, and in U.S. Pat. No. 6,680,166 of Mullon et. al. Another type of bioreactor, described in U.S. Pat. No. 6,979,308 of MacDonald et al., includes concentric hollow fibers of increasing diameter, one within the other. Within the spaces defined by the hollow fibers are defined spaces for medium flow, gas delivery, and cell growth. Such reactors deigned to improve gas delivery can be complex in design and operation, and may further be limited in the amount of gases that can be delivered to the cells in the extra-capillary space.

Therefore, there may be a need to provide method, device and/or apparatus that can provide improved transfer and control of gases and media to cells in a bioreactor. These and other objects, features and advantages of the present disclosure will become apparent upon reading the following detailed description of exemplary embodiments of the disclosure.

SUMMARY OF EXEMPLARY EMBODIMENTS

Embodiments of the present disclosure generally relate to systems, methods, and apparatus for a hollow-fiber bioreactor, where the bioreactor is configured to provide flow of both liquid nutrient-containing media and separate gas compositions through a plurality of permeable hollow fibers. This facilitates improved control of the environment surrounding the growing cells outside of the hollow fibers, including improved oxygenation in certain systems arising from the direct flow of gas through the lumens, and may facilitate introduction and/or extraction of both liquid-based (e.g., aqueous) and gaseous components via the hollow fibers.

The bioreactor can include an enclosed chamber containing one or more hollow fibers therein. An extra-capillary space can be defined as the volume within the chamber that lies outside of the walls of the fibers. Cells can be provided in the extra-capillary space in an appropriate environment (e.g., in an aqueous solution) to promote their vitality and growth. Some or all of the cells may optionally attach or adhere to the outer surface of the fibers. The chamber can include one or more access ports to facilitate introduction or removal of materials (e.g., cells, solutions, or the like) to or from the extra-capillary space. Flowing both liquids and gases through the same fiber lumens can provide more direct supply of substances to cells proximal to or adherent to the outer surfaces of the fibers, and can also improve spatial homogeneity of the environment in the extra-capillary space, which can lead to improved cell vitality and growth conditions.

The hollow fibers can be configured such that their central lumens are in fluid communication with one or more external reservoirs or conduits, e.g., via couplers, nozzles, openings, or the like provided at or near the ends of the chamber. The fiber ends can be supported by potting structures or the like to hold the fibers in place and to provide separation of the lumens at the fiber ends from the extra-capillary space. Accordingly, liquids and gases can flow through the fiber lumens from external reservoirs or conduits without being introduced directly into the extra-capillary space.

The fiber walls can be made of a permeable material, which can be selected to allow liquid media (or certain components thereof) and gases to transfer from the fiber lumens into the extra-capillary space, and optionally to allow certain cell waste products and/or by-products, which may include gaseous substances, to transfer from the extra-capillary space into the fiber lumens through the fiber walls. The permeable material can also be selected such that it prevents transfer of cells from the extra-capillary space into the lumens of the fibers. In certain embodiments, the permeable material includes pores having effective diameters that are not larger than 0.2 microns. In various embodiments, the permeable material can be made of one or more of polysulfone, modified polysulfone, polyvinyledine fluoride, cellulose acetate, acrylic copolymer, and/or a cellulose derivative, where the cellulose derivative can be, e.g., one or a mixed ester of cellulose and cupra-ammonium rayon.

The diameter of the fiber lumens can be, e.g., between about 500 and 1000 microns to facilitate gravity-driven flows therethrough. Smaller fiber diameters can be used, e.g., if a mechanical pumping arrangement or the like is used to drive such flows. The fiber wall materials can be selected based on the desired transport properties of particular substances through them.

One or more reservoirs can be provided in fluid communication with the lumens at each end of the fibers, e.g., via tubing, conduits, or the like. The reservoirs (or the internal surface thereof) are preferably made of gas-impermeable and non-reactive materials. In certain embodiments, at least a portion of the reservoirs can be flexible or deformable, e.g., to accommodate volume changes of the enclosed contents, and/or to expel liquid or gas therefrom when applying a pressure or mechanical force to an outer surface of the reservoirs. In further embodiments, the reservoirs can be rigid, and flow of liquids or gases into or out of them can be achieved using an external pump arrangement. The reservoirs can be provided with one or more access ports to facilitate introduction and/or removal of liquid media and/or gases to or from their interior volumes.

One or more sensors can be provided in the reservoirs, chamber, extra-capillary space, tubes or ducts connecting the reservoirs to the fiber lumens, etc. Such sensors can include, but are not limited to, temperature sensors, pressure sensors, flow sensors, pH sensors, oxygen ($O_2$) sensors, glucose sensors, capacitance sensors, or the like. Such sensors can be configured to provide signals to monitor process parameters, e.g., to generate a display of detected parameters and/or conditions during operation of the bioreactor system. Such signals can also be directed to one or more control components (e.g., supply valves, heaters, pumps) to provide feedback control of conditions in the system.

In certain embodiments, flow of liquid media and/or gas can be gravity-driven, e.g., based on the elevation of one or more reservoirs relative to the chamber containing the hollow fibers and extra-capillary space. The chamber can optionally be tilted during operation to provide certain process advantages. Any one of various mechanical pumping arrangements can be used in further embodiments to controllably flow liquid media and gases through the fibers. Such pumping arrangements can include, e.g., conventional fluid pumps or pistons, devices configured to controllably deform or squeeze the one or more deformable reservoirs, etc. Both gas and liquid media can be provided in a single reservoir, or they may be provided in separate reservoirs. Valves and/or other conduit configurations can be provided to controllably direct and control flows of liquid media and gas through the hollow fibers and into or out of the one or more reservoirs. The flow direction of such fluids can be reversed during operation, e.g., to improve homogeneity of conditions within the extra-capillary space.

BRIEF DESCRIPTION OF THE DRAWINGS

Further objects, features and advantages of the disclosure will become apparent from the following detailed description taken in conjunction with the accompanying figures showing illustrative examples, results and/or features of the exemplary embodiments of the present disclosure, in which.

The various embodiments of the disclosure are described herein with reference to the figures, where like reference numbers indicate identical or functionally similar elements. Further features and advantages of the disclosure as well as the structure and operation of various embodiments of the present disclosure are described in detail below with reference to the accompanying drawings. To the extent that the present disclosure does reference the figures, it is done so in connection with the illustrative embodiments and is not limited by the particular embodiments illustrated in the figures. It is intended that changes and modifications can be made to the described embodiments without departing from the true scope and spirit of the present disclosure.

DETAILED DESCRIPTION OF EXEMPLARY EMBODIMENTS

Figure 1:
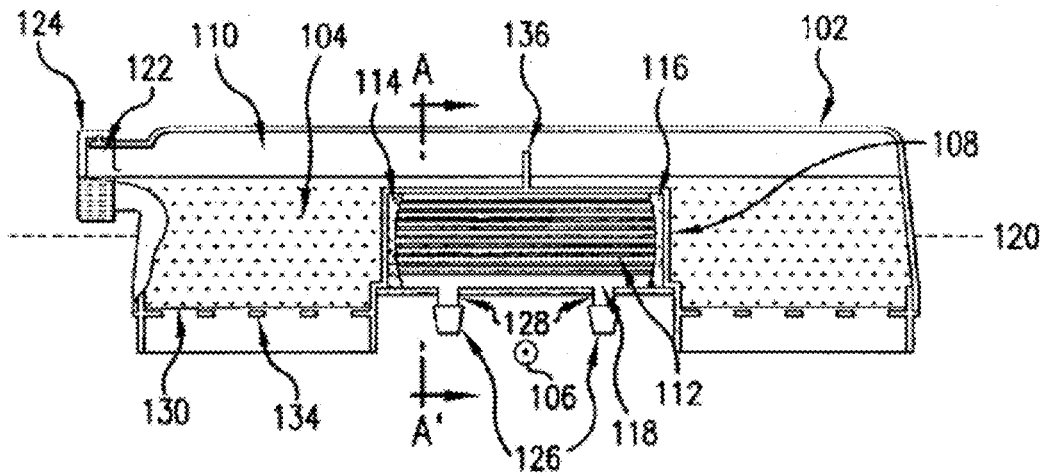
FIG. 1 is a cutaway, cross sectional side view of an exemplary prior art hollow-fiber bioreactor system.
Figure 2:
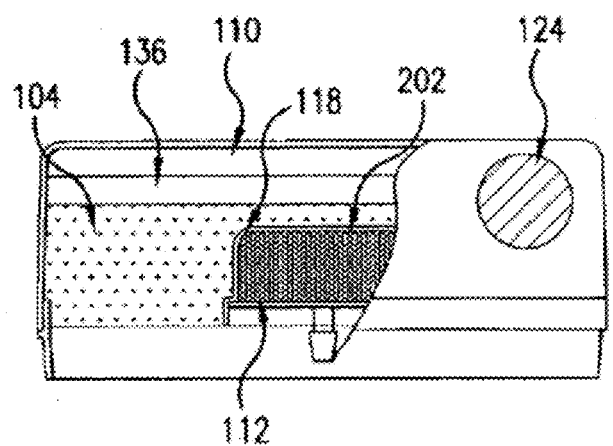
FIG. 2 is a cutaway end view showing a partial cross section of the bioreactor shown in FIG. 1 taken along section A-A'.
Figure 3:
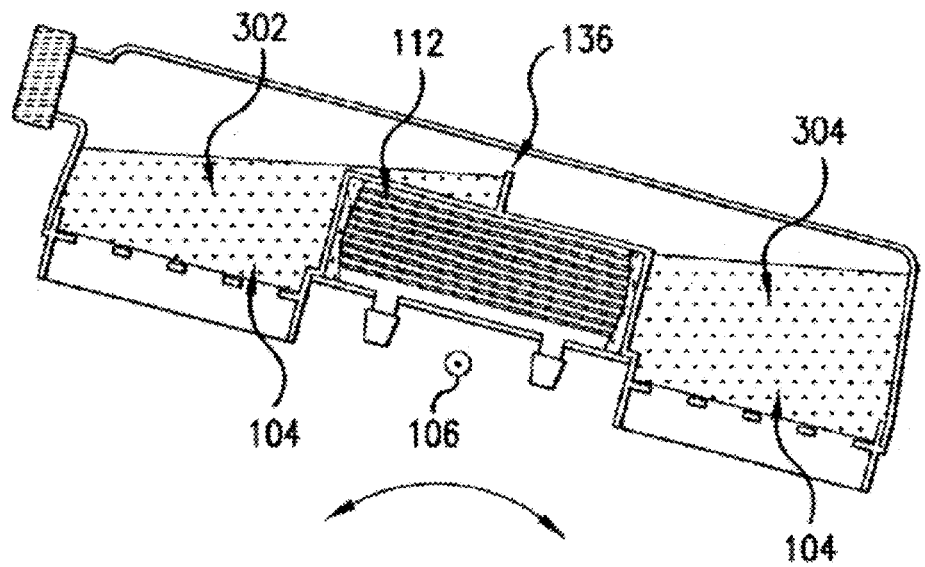
FIG. 3 is an illustration of cell-culture media flow induced by a rocking motion of the prior art bioreactor shown in FIG. 1.
Figure 4:
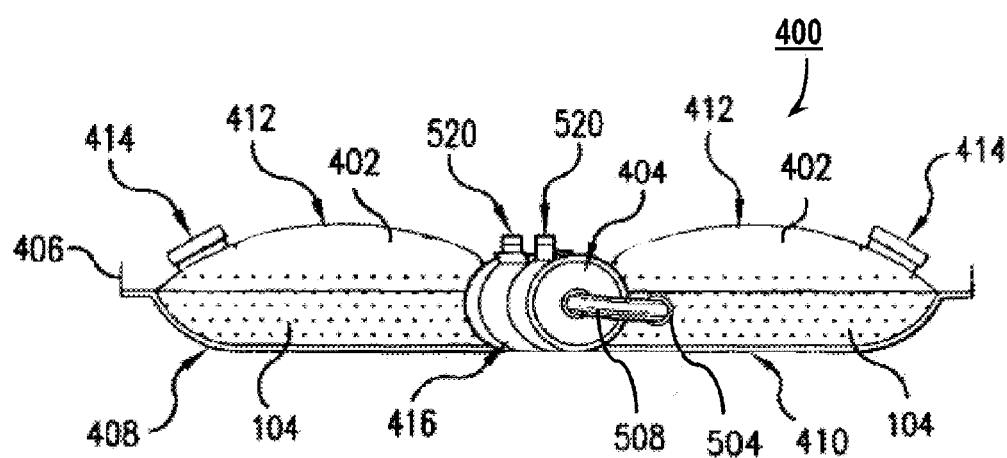
FIG. 4 is a side view of a bioreactor apparatus in accordance with certain embodiments of the present disclosure.
Figure 5:
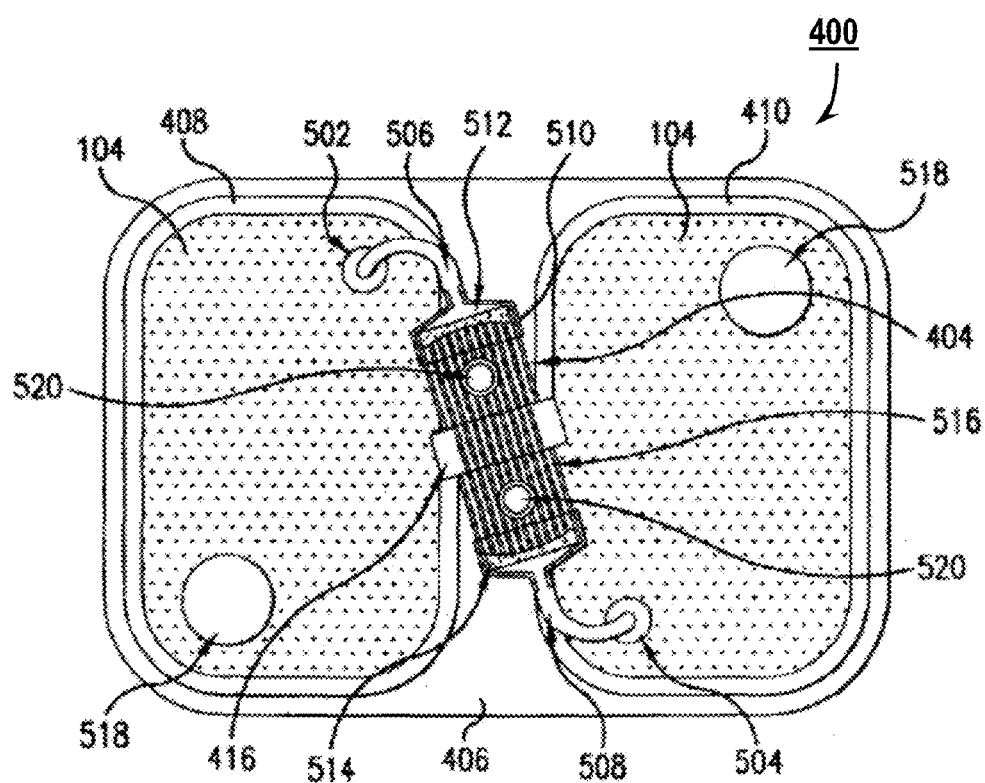
FIG. 5 shows a top view of the bioreactor apparatus shown in FIG. 4.

FIG. 4 is a side view of an exemplary configuration of a hollow-fiber bioreactor system 400 in accordance with certain embodiments of the present disclosure, and FIG. 5 shows a top view of this same bioreactor system 400. An enclosed reactor chamber 404 is provided that includes a plurality of hollow fibers 510 passes therethrough. For example, the enclosed chamber 404 can be a standard, commercially available shell-and-tube type bioreactor designed for use with an external circulating system. The chamber volume can be, e.g., up to about one liter or more. Because of the higher densities of cell cultures that can be maintained, as described below, the production capacity of such a volume can be equivalent to that of a conventional stirred tank system having a volume of about 100 liters.

A first media reservoir 408 and second media reservoir 410 can be adapted to contain cell-culture media 104 and gas 402 in a headspace 412 above the media 104, e.g., in an upper portion of the media reservoirs 408, 410. The first media reservoir 408 can be provided with a first port 502, and the second media reservoir 410 can be provided with a second port 504. The media reservoirs 408, 410 can be provided in fluid communication with the lumens of the fibers 510, such that a flow of the media 104 and/or gas 402 can be provided from the first media reservoir 408 through the first port 502, through the hollow fibers 510 provided in the chamber 404, and into the second media reservoir 410 through the second port 504. The bioreactor system 400 can also permit flow of media 104 and/or gas 402 in the opposite direction, viz., from the second media reservoir 410 through the hollow fibers 510 and into the first media reservoir 408. The connections can be provided by various configurations including, but not limited to, a first tube 506 connected between first port 502 and enclosed chamber 404, and a second tube 508 connected between second port 504 and enclosed chamber 404. In certain embodiments, the reservoirs 408, 410 can be coupled directly to the ports 502, 504, e.g., they can be attached directly thereto or formed as extensions at opposing ends of the chamber 404, or can be connected by rigid ducts or manifolds.

The tubes 506, 508 and/or reservoirs 408, 410 can be flexible in certain embodiments, or rigid in further embodiments. The tubes 506, 508 and reservoirs 408, 410 (as well as other system components that transport or contain fluids and/or gases) are preferably formed of or coated with a gas-impermeable, inert material that is nonreactive and biocompatible, such as, e.g., Teflon® or the like. For example, the reservoirs 408, 410 can be flexible bags such as Thermo Scientific HyClone BPCs employing CX5-14, a pentalaminate animal component-free film, which are gas-impermeable. Such a material allows the gas composition inside the bags to be tightly controlled for optimum cell culture performance. Other conduits or fluid transport arrangements can also be provided between these components.

In certain embodiments, a tray 406 can optionally be included to provide mechanical or structural support to the reservoirs 408, 410 and/or the reactor chamber 404. A clip 416 or other mounting arrangement can optionally be provided to attach or affix the enclosed chamber 404 to the tray 406. Other arrangements can also be used to hold the chamber 404 in an appropriate position with respect to the media reservoirs 408, 410. In further embodiments, the reservoirs 408, 410 and/or the reactor chamber 404 can be provided with individual supporting structures that can facilitate their manipulation and positioning.

The fibers 510 can be secured at or near their ends by a first potting structure 512 and a second potting structure 514. An extra-capillary space 516 can be defined as the volume between an interior of the enclosed chamber 404 and the exterior surfaces of the hollow fibers 510. Such potting structures 512, 514 can support the ends of the fibers 510, and provide a barrier between the extra-capillary space 516 and the end portions of the chamber 404 that include the ports 502, 504. Each hollow fiber 510 includes a lumen provided in fluid communication with the reservoirs 408, 410, for example, via the first port 502 and second port 504, such that the fiber lumens are open to the flow of cell-culture media 104 and/or gas 402 therethrough, e.g., between ports 502, 504. In this configuration, cell-culture media 104 and gas 402 can pass through the lumen of hollow fiber 510 between the reservoirs 408, 410 without directly entering or contacting the extra-capillary space 516. Instead, nutrients or other components in the media 104 and gas 402 can pass through the walls of hollow fiber 510 to nourish the cells in the extra-capillary space 516, e.g., the volume within the chamber 404 that is outside of the hollow fibers 510. This indirect exposure of the cells to the media 104 and gas 402 can avoid subjecting the cell environment to significant variations in primary and secondary metabolites (such as glucose and lactate), oxygen, or product levels. Other functions and parameters of the hollow fibers 510 are described in more detail herein.

For example, in certain exemplary embodiments, between about 20 and about 4000 hollow fibers 510 can be disposed within the enclosed chamber 404. In certain embodiments, larger numbers of fibers 510 may be used, e.g., in bioreactors 400 having a larger enclosed chamber 404. The adaptation of the fibers 510 to flow both media 104 and gases 402 through them can facilitate the use of bioreactors having such larger volumes, because they can better support transport of various necessary or desirable substances to and from the cell cultures contained therein. The length of the hollow fibers 510 can generally be between about 10 cm and about 50 cm, which can provide an appropriate length for controllable flow of fluids (e.g., media 104 and/or gas 402) through the central lumen at relatively low pressure differentials or other fluid driving forces. Other lengths may be used in further embodiments, e.g., longer fibers 510 can be used in embodiments wherein the liquid media 104 is forced through the fibers 510 using a pumping arrangement or other pressure-driven arrangement. Although the exemplary fibers 510 are illustrated as being straight in FIG. 5, they can optionally be provided with a plurality of curves, e.g., in a continuously, undulating shape, which can promote a more uniform spatial distribution of the fibers 510 within the chamber 404 while facilitating flow through the lumens.

The diameter of the hollow fibers 510 can preferably be between about 500 microns and about 1,000 microns. Such diameters are small enough that they can provide a sufficiently large surface area density within the chamber 404, while also being large enough to facilitate flow of liquids (such as the media 104) through the central lumens. For example, the hollow fibers 510 may have a length-to-diameter ratio of less than about 170:1 to reduce the head loss of cell-culture media 104 that passes through them, e.g., in embodiments where the flow of fluids through the fibers 510 is gravity-driven. Larger fiber length-to-diameter ratios (e.g., fibers 510 that are longer and/or have smaller diameters) may be used in embodiments where the liquid media 104 and/or gas 402 are forced through the lumens of the hollow fibers 510 using pressure-driven arrangements such as those described herein.

Cumulatively, the hollow fibers 510 in the exemplary bioreactor 400 can be configured to support a typical flow rate of cell-culture media 104 that is, e.g., between about 5 ml/min and about 100 ml/min. Overall flow rates that are larger or smaller than this range can be used in certain embodiments and can be selected, e.g., based on the overall size of the reactor chamber 404 and volume of the extra-capillary space 516, the compositions of the media 104 and gas 402, the types of cells provided in the extra-capillary space 516, etc. The number, size, and spacing of the hollow fibers 510 can be selected to provide a total fiber surface area density that is as large as 100 cm^2 per ml or greater per unit volume of extra-capillary space 516 within the enclosed chamber 404. In further exemplary embodiments of the present disclosure, hollow fibers 510 can be provided in greater or fewer numbers than those described above, and they may have lengths and/or diameters that vary from the ranges described above. For example, the properties of the hollow fibers 510 can be generally selected to provide sufficiently large total surface area, sufficiently small inter-fiber spacing, and sufficiently large lumen diameter to facilitate efficient flow of fluids through the fibers 510 and sufficient transport of nutrients, gases, by-products, waste products, etc., between the lumens of the fibers 510 and the extra-capillary space 516 for a particular size and shape of the chamber 404.

The fibers 510 can be made at least partially of a permeable material, which can be selected to allow liquid media 104 (or certain components thereof) and gas 402 to transfer from the fiber lumens into the extra-capillary space 516, and optionally to allow certain cell waste products and/or by-products, which may include gaseous substances, to transfer from the extra-capillary space 516 into the fiber lumens through the fiber walls. The permeable material can also be selected such that it prevents transfer of cells from the extra-capillary space 516 into the lumens of the fibers 510. In certain embodiments, the permeable material includes pores having effective diameters that are not larger than 0.2 microns. In various embodiments, the permeable material can be made of one or more of polysulfone, modified polysulfone, polyvinyledine fluoride, cellulose acetate, acrylic copolymer, and/or a cellulose derivative, where the cellulose derivative can be, e.g., one or a mixed ester of cellulose and cupra-ammonium rayon. Other fiber materials may be used in further embodiments that have such functional properties described herein with respect to particular cells, media 104, gas 402, etc. For example fiber materials having a particular average pore size or pore size range, biochemical inertness, surface properties, and the like can be selected that facilitate transport of certain substances (e.g. nutrients or waste products) between the fiber lumen and the extra-capillary space 516, while inhibiting such transport of other components or entities such as cells. Fiber materials having such properties can be selected based, e.g., on conventional techniques, published data, specific cell cultures and/or cellular products for a particular use, and/or other knowledge available to and understood by one of ordinary skill in the relevant art.

The hollow fibers 510 are typically formed of a permeable material. The permeable material allows nutrients in the cell-culture media 104 and/or metabolizing gases 402 to pass from the central lumens of the hollow fibers 510 through the walls of the hollow fibers 510 and into the cells in the extra-capillary space 516. The permeable material can further facilitate transport of certain cell waste products and/or gaseous waste products from the extra-capillary space 516 through the walls of the hollow fibers 510 to the cell-culture media 104 and/or gas 402 that is flowing through the lumens, while retaining the cells and larger secreted products within the extra-capillary space 516.

Each of the media/gas reservoirs 408, 410 can be provided with one or more openings 518, as shown in FIG. 5. The opening 518 can facilitate access to the interior of the reservoirs 408, 410, e.g., to allow fresh cell-culture media 104 and/or fresh gas 402 to be supplied to the media reservoirs 408, 410, to facilitate removal of stale cell-culture media 104 and/or stale gases 402 to be removed from the reservoirs 408, 410, and/or to allow easy removal of cell waste products from reservoirs 408, 410. A cap 414 can be provided on each opening 518, as shown in FIG. 4, to prevent contamination of the interior volumes of the reservoirs 408, 410 by the surrounding environment, and to maintain an applied pressure or vacuum within the reservoirs 408, 410. Various tubes, conduits, valves, or other arrangements (not shown) can also be provided in communication with the openings 518, e.g., coupled or connected to caps 414, to facilitate introduction or removal of various substances from the reservoirs 408, 410. Other access points can be provided at further locations in the bioreactor system 400, e.g., to facilitate introduction and/or removal of media 104, gas 402, or the like from the system. For example, access ports, valves, or the like can be provided at one or more of tubes 506, 508, caps 414, the ends of chamber 404, etc.

The reservoirs 408, 410 can optionally be provided with one or more sensor arrangements to facilitate monitoring and control of the compositions of the media 104 and/or gas 402 therein. For example, sensors for such parameters as, e.g., pH, O2, and/or glucose values or levels/concentrations can be provided to facilitate near-real-time monitoring of the culture environment. The absence of cells in the reservoirs 408, 410 being monitored can supports more robust and sensitive measurements. Signals provided by such sensors can be used together with conventional control arrangements (not illustrated) to facilitate control and/or adjustment of medium and gas properties and compositions in the media bags, and/or to vary flow rates through the fibers 510, to affect the environment in the extra-capillary space 516 that contains cultured cells. Other types of sensors can also be used in further embodiments, including capacitance-based monitoring probes or the like. For example, passive electrical (dielectric) radio frequency-based sensors can be provided to measure the overall capacitance, and therefore viability, of the cell mass within the extra-capillary space 516 of the chamber 404.

The relatively small volume of both the chamber 404 and the medium 104 that is present in the bioreactor at any one time facilitates a more precise and responsive monitoring and process control, even though the bioreactor system 400 may support a flow of as much as 50-100 liters per day or more of the culture media 104 therethrough. Pressure sensors (not shown) and/or pressure relief valves (not shown) may also be provided at one or more locations of the bioreactor system 400, e.g., on tubes 506, 508, reservoirs 408, 410, on chamber 404 (e.g., in communication with the extra-capillary space 516. Such pressure sensors or valves may be used to limit pressure build-up within various portions of the bioreactor system 400. They may also be used in conjunction with a control arrangement (not shown) provided in communication with any of the various arrangements configured to flow fluids (e.g., media 104 and/or gas 402) through portions of the bioreactor systems that described in the other embodiments herein.

The chamber 404 can be provided with one or more access ports 520 in communication with the extra-capillary space 516 within the chamber 404. The access port 520 can facilitate, for example, placement of developing cells into the extra-capillary space 516, removal of mature cells from the extra-capillary space 516, harvesting of secreted products to be harvested from the extra-capillary space 516, and/or introduction of certain substances (e.g., reagents, drugs, and/or DNA or RNA vectors) into the extra-capillary space 516 to treat the cells therein or to modify their environment directly.

Exemplary embodiments of the present disclosure can provide a simple and effective system and method for producing and maintaining a controlled environment for cellular growth and propagation in a bioreactor. For example, the exemplary hollow-fiber bioreactor 400 shown in FIGS. 4 and 5 can be used to circulate both cell-culture media 104 and gas 402 from one reservoir 408 through the hollow fibers 510 and into the other reservoir 410. Further, the direction of flow can be reversed cyclically such that the cell-culture media 104 and gas 402 then flow from the reservoir 410 back to reservoir 408. Such changes in flow directions can further homogenize the environment throughout the extra-capillary space 516 containing the cells, e.g., to reduce or avoid significant compositional gradients or differences along the length of the chamber 404.

The gas 402 in the headspace 412 of the reservoirs 408, 410 can include oxygen and/or other gaseous components that can facilitate growth of cells and/or production of certain cellular by-products in the extra-capillary space 516 of the bioreactor 400. As the gas 402 flows through the hollow fibers 510, it may readily penetrate the permeable walls of the hollow fibers 510 and enrich the surrounding extra-capillary space 516 that contains the growing cells. Gas 402 flowing through the fibers 510 can also facilitate withdrawal of gaseous cell by-products from the extra-capillary space 516. Composition of the gas 402 in the reservoirs 408, 410 can be monitored using conventional sensors or the like. The gas composition can also be altered by introducing or withdrawing portions of the gas 402 to or from the reservoirs 408, 410, e.g., via the opening 518.

Figure 6A:
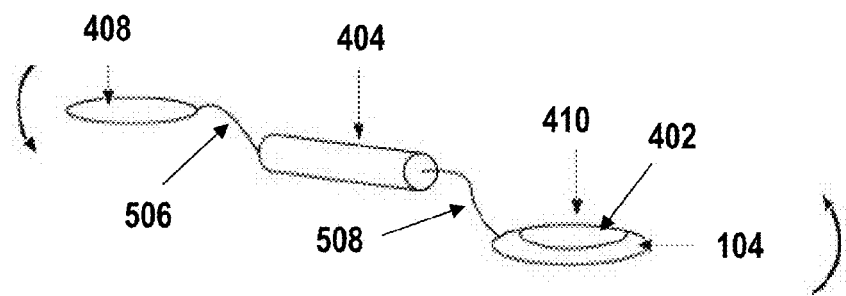
FIGS. 6A-6D illustrate a sequence of operation for a gravity-driven bioreactor apparatus in accordance with certain embodiments of the present disclosure.

In one exemplary embodiment, flow of the media 104 and gas 402 through the bioreactor can be induced via gravitational forces, as shown schematically in FIGS. 6A-6D. In FIG. 6A, an initial configuration of the bioreactor system is shown, which includes the chamber 404 containing the hollow fibers 510 (not shown), and reservoirs 408 and 410 provided in communication with the hollow fibers 510 within the chamber 404, via tubes 506 and 508, respectively, as described above.

Figure 6B:
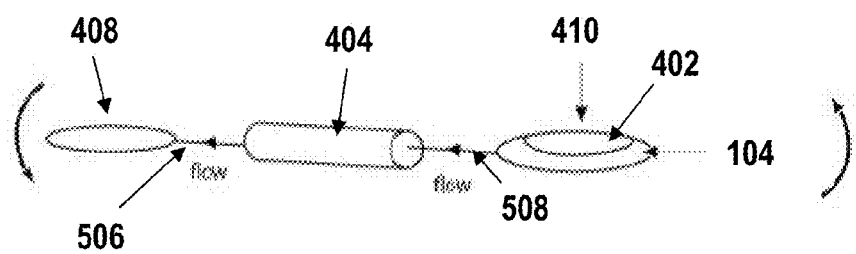
Figure 6C:
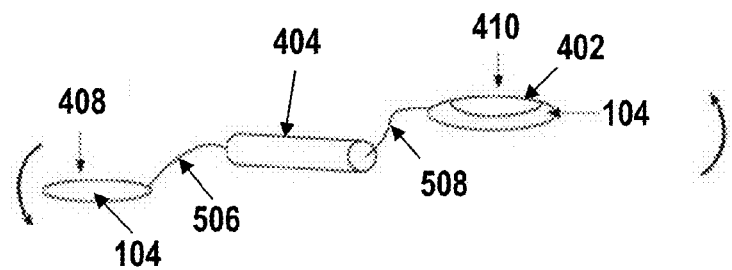
Figure 6D:
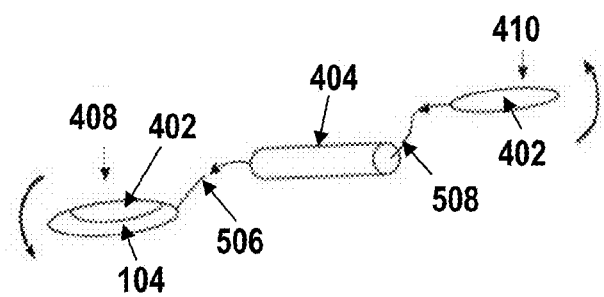

As shown in FIG. 6A, the reservoir 408 can be initially empty or substantially so, although it may contain small quantities of the media 104 and/or gas 402. The reservoir 410 initially contains a quantity of the media 104 and gas 402. As the reservoir 410 is elevated relative to the chamber 404 and reservoir 408, flow of the media through tube 508 and through the hollow fibers 510 in the chamber 404 begins, as shown in FIG. 6B. When the reservoir 410 is further elevated, as shown in FIG. 6C, flow of the media 104 through the hollow fibers 510 continues, and the media 104 continues flowing through tube 506 and into the reservoir 408. When the media 104 has flowed out of the reservoir 410, some of the gas 402 initially provided in the reservoir 410 will be drawn through the hollow fibers 510 and then flow through tube 506 and into reservoir 408, as shown in FIG. 6D. This entire process can then be reversed, by elevating reservoir 408 relative to the chamber 404 and lowering reservoir 410, to generate sequential flow of the media 104 and gas 402 through the hollow fibers 510 in the opposite direction. In this manner, controlled, alternating flows of the media 104 and gas 402 through the hollow fibers 510 in the chamber 404 can be achieved.

In further embodiments, the reservoirs 408, 410 can be partially or fully deformable, e.g., they can be formed using flexible materials such as a plastic or polymer. A compressive force or pressure can then be applied, e.g., to the deformable walls of the reservoir 410 in FIGS. 6C and 6D, to enhance and/or further drive the flow of media 104 and/or gas 104 through tube 508, the hollow fibers 510 in the chamber 404, tube 506, and into reservoir 408. For example, the flow rate of media 104 and/or gas 402 through the bioreactor can be controlled, in whole or in part, by controlling the amount of force used to compress reservoir 410. A similar force or pressure can then be applied to the reservoir 408 during the subsequent reverse cycle, when media 104 and/or gas 104 flow through the bioreactor from reservoir 408 to reservoir 410. Various arrangements and methods for controlling or modifying the flow of these fluids through the bioreactor are described below in further embodiments of the present disclosure.

The flow of media 104 and gas 402 through the bioreactor as shown in FIGS. 6A-6D can provide liquid-based nutrients or other substances, as well as gaseous components, to the extra-capillary space 516. Certain aqueous and/or gaseous cellular waste products or by-products can also be removed from the extra-capillary space 516 by diffusing through the walls of the hollow fibers 510 and being carried away by the flowing media 104 and/or gas 402 in the central lumen of the fibers 510.

Figure 7:
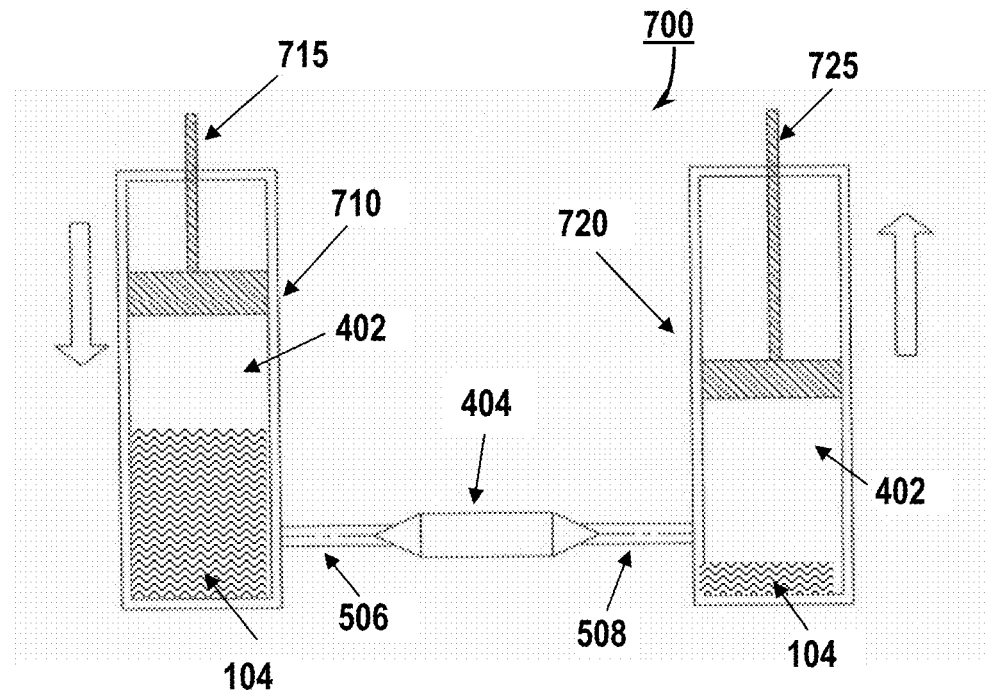
FIG. 7 is a schematic illustration of a bioreactor apparatus in accordance with further embodiments of the present disclosure.

FIG. 7 illustrates a hollow-tube bioreactor system 700 in accordance with further exemplary embodiments of the present disclosure. The bioreactor system 700 includes a chamber 404, as described above, which contains a plurality of hollow fibers 510 (not shown). Opposite ends of the central lumens of the fibers 510 are in fluid communication with tubes 506, 508, as described above. The interior volume of a first piston chamber 710 is coupled to the tube 506. The first piston chamber 710 includes a first piston 715 that is movable therein. Similarly, the interior volume of a second piston chamber 720 is coupled to the tube 508, and includes a second movable piston 725.

Initially, the first piston chamber 710 contains both gas 402 and cell-culture media 104. During operation, the first piston 715 can be advanced into the first piston chamber 710 to direct flow of the media 104 through the hollow fibers 510 in the chamber 404. As the first piston 715 continues to advance, the media 104 is mostly or fully expelled from the first piston chamber 710 (depending on where the tube 506 is coupled to the first piston chamber 710). Gas 402 is then forced through the bioreactor and into the second piston chamber 720. The second piston 725 can be simultaneously withdrawn from the second piston chamber 720, e.g., at a rate similar to that of the advancing first piston 715, to provide better control of fluid flow rates and/or to avoid excessive pressure changes within the tubes 506, 508 and hollow fibers 510. Optionally, the second piston 725 can be allowed to move freely with no applied force. In further embodiments, the second piston 725 can be withdrawn to "pull" the gas 402 and/or liquid media 104 through the bioreactor from the first piston chamber 710.

After the first piston 715 has advanced to a desired extent, the flow cycle can be reversed by advancing the second piston 725 and/or withdrawing the first piston 715, to generate sequential flow of media 104 and gas 402 through the bioreactor in the opposite direction. This cycle can be repeated continuously for any desired duration. Access ports (not shown) can optionally be provided in the walls of the piston chambers 710, 720, which can facilitate introduction and/or removal of media 104, gas 402, specific substances, and/or products generated within the bioreactor from the piston chambers 710, 720. Appropriate valves, caps, or the like can also be provided, e.g., in the walls of the chambers 710, 720, to facilitate intermittent or continuous access to the interior of these piston chambers 710, 720.

In a further embodiment, the orientation of the piston chambers 710, 720 can be reversed vertically, such that the tubes 506, 508 are coupled to the upper portions of the chambers 710, 720, and the pistons 715, 725 enter them from below. Horizontal or angled orientations of the piston chambers 710, 720 can also be used in still further embodiments of the disclosure.

The fluid flow velocities through the bioreactor system 700 can be controlled, e.g., by controlling the advancement and withdrawal rates of the pistons 715, 725. The absolute and relative durations of the flow of media 104 and gas 402 through the bioreactor can be determined, e.g., by the amounts of media 104 and gas 402 provided in the chambers 710, 720, the extent of advancement and withdrawal of the pistons 715, 725 during a flow cycle, and the location where the tubes 506, 508 are coupled to the piston chambers 710, 720.

Figure 8:
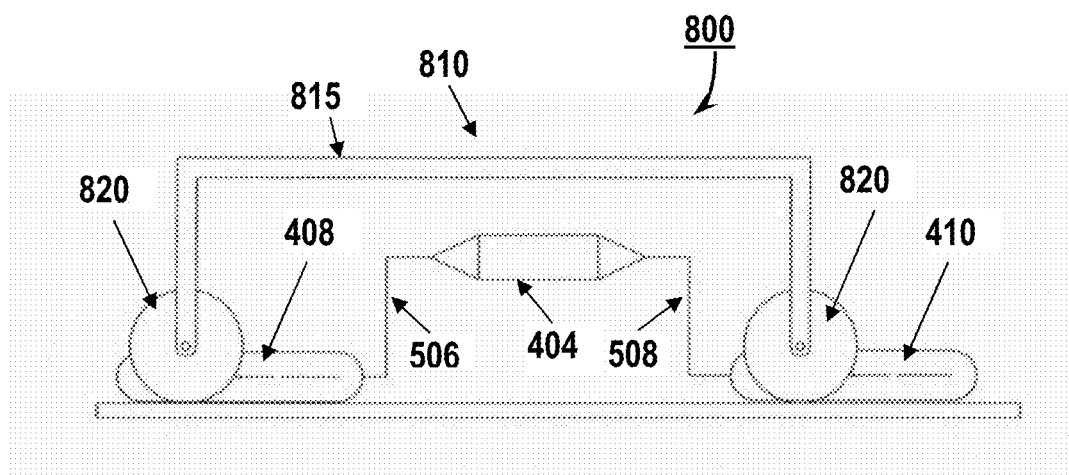
FIG. 8 is a schematic illustration of a bioreactor apparatus in accordance with still further embodiments of the present disclosure.

A hollow-tube bioreactor system 800 in accordance with further exemplary embodiments of the present disclosure is shown in FIG. 8. The bioreactor system 800 includes a chamber 404, as described above, which contains a plurality of hollow fibers 510 (not shown). Opposite ends of the central lumens of the fibers 510 are in fluid communication with tubes 506, 508, as described above. The interior volume of a first reservoir 408 is coupled to the tube 506, and the interior volume of the second reservoir 410 is coupled to the tube 508. The reservoirs are formed at least partially of a deformable material, e.g. as described above, and contain cell-culture media 104 and/or gas 402 (not shown). The bioreactor system 800 further includes a roller arrangement 810 that includes a support frame 815 that is coupled to two rotatable rollers 820. The rollers 820 can be provided in contact with the reservoirs 408, 410 as shown in FIG. 8.

During operation, the roller arrangement 810 can be moved laterally with respect to the reservoirs 408, 410 (e.g., left-to-right in FIG. 8) to expel the media 104 and/or gas 402 from reservoir 408 through the hollow fibers 510 in the chamber 404 and into the reservoir 410. The roller arrangement 810 can be advanced until the contents of the reservoir 408 are mostly or fully expelled through the bioreactor and into the second reservoir 410. The roller arrangement can then be moved in the opposite direction, to expel the media 104 and/or gas 402 from reservoir 410 through the hollow fibers 510 in the chamber 404 and into the reservoir 408. A conventional translating arrangement or the like (not shown) can be provided to controllably move the roller arrangement 810 in a particular direction and/or at one or more particular speeds. Appropriate valves, caps, or the like (not shown) can also be provided, e.g., in the walls of the reservoirs 408, 410, to facilitate access to their interiors as described above.

The order of flow of liquid media 104 and gas 402 can be determined, e.g., by the location where the tubes 506, 508 are coupled to the reservoirs 408, 410. For example, with the general orientation shown in FIG. 8, coupling the tubes 506, 508 to a lower portion of the reservoirs 408, 410 would cause the denser media 102 to be initially forced or 'squeezed' from the reservoir 408 through the bioreactor. When the media 102 is substantially depleted, the gas 402 remaining in the reservoir 408 would then be expelled through the bioreactor. In a further embodiment, the tubes 506, 508 may be coupled to an upper portion of the reservoirs 408, 410. This would cause the gas 402 in the reservoir 408 to be expelled through the bioreactor first, followed by the media 104. Other orientations and configurations of the reservoirs 408, 410 and roller arrangement 810 can be used in further embodiments. For example, the orientation of these components need not be horizontal as shown in FIG. 8, but can be oriented vertically or at some other angle.

In a still further embodiment, the roller arrangement 810 may be configured such that only a single roller 820 contacts one of the reservoirs 408, 410 at any time. In such embodiment, the single roller 820 will expel the fluids from a single reservoir 408, 410, and then a single roller 820 (e.g., the same roller 820 or a different one) will expel fluids from the other reservoir 410, 408.

Figure 9:
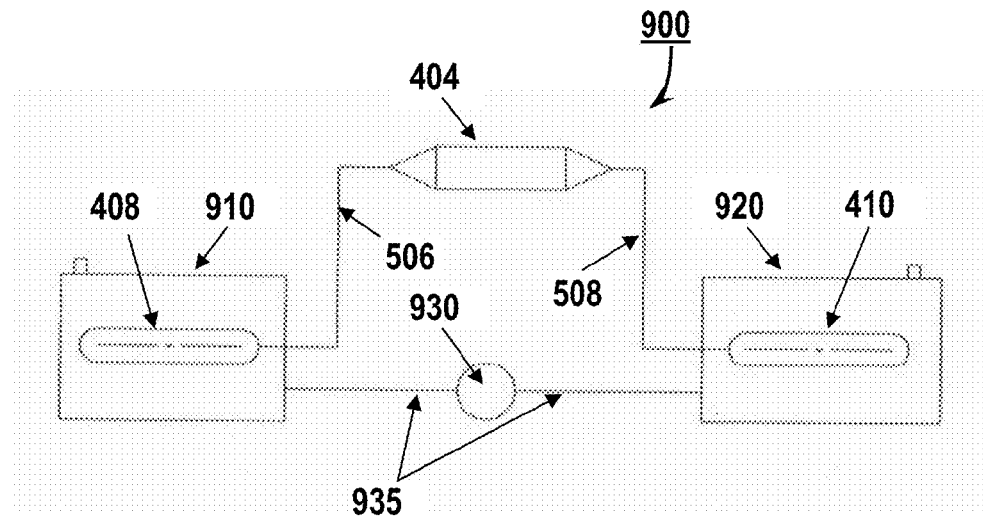
FIG. 9 is a schematic illustration of a bioreactor apparatus in accordance with yet further embodiments of the present disclosure.

FIG. 9 illustrates a hollow-tube bioreactor system 900 in accordance with still further exemplary embodiments of the present disclosure. The bioreactor system 900 includes a chamber 404, as described above, which contains a plurality of hollow fibers 510 (not shown). Opposite ends of the central lumens of the fibers 510 are in fluid communication with tubes 506, 508, as described above. The interior volume of a first reservoir 408 is coupled to the tube 506, and the interior volume of a second reservoir 410 is coupled to the tube 508. The reservoirs are formed at least partially of a deformable material, e.g. as described above, and contain cell-culture media 104 and/or gas 402 (not shown). The bioreactor system 900 further includes enclosures 910, 920 that contain reservoirs 408 and 410, respectively. A pump arrangement 930 is also provided that is coupled to the interior volumes of the enclosures 910, 920 via conduits 935. Appropriate valves, caps, or the like (not shown) can also be provided, e.g., in the walls of the reservoirs 408, 410 with access from the exterior of enclosures 910, 920, to facilitate access to the contents of the reservoirs 408, 410 as described above.

The pump arrangement 935 can be configured to vary the pressure within the enclosures 910, 920, e.g., to provide an elevated pressure and/or a reduced pressure, e.g., a partial vacuum. Conventional valve arrangements and control arrangements can further be provided such that the pressure within each of the enclosures 910, 920 can be separately varied and/or maintained. During operation, the pump arrangement 935 can be controlled to first elevate the pressure in enclosure 910 relative to the pressure in enclosure 920. This pressure difference surrounding the reservoirs 408, 410 can cause the fluids (e.g., media 104 and gas 402) to be expelled from the reservoir 408, through the hollow fibers 510 in the chamber 404, and into reservoir 410 via tubes 506 and 508. The pump arrangement 935 can then be configured and controlled to elevate the pressure in enclosure 920 relative to the pressure in enclosure 910, to expel media 104 and gas 402 from the reservoir 410, through the bioreactor, and into reservoir 408. This cycle can be repeated to provide alternating flows of media 104 and gas 402 through the bioreactor.

Similar to the exemplary system 800 shown in FIG. 8, the order of expulsion of liquid media 104 and gas 402 from each of the reservoirs 408, 410 can be determined by where the tubes 506, 508 attach or couple to the reservoirs 408, 410. For example, a tube coupling point at or near the bottom of a reservoir will lead to liquid media 104 being expelled first, followed by the gas 402. Conversely, a tube coupling point at or near the top of a reservoir will lead to gas 402 being forced from the reservoir before the liquid media 104. Either configuration may be used, e.g., based on particular needs and configuration of the overall system.

Figure 10:
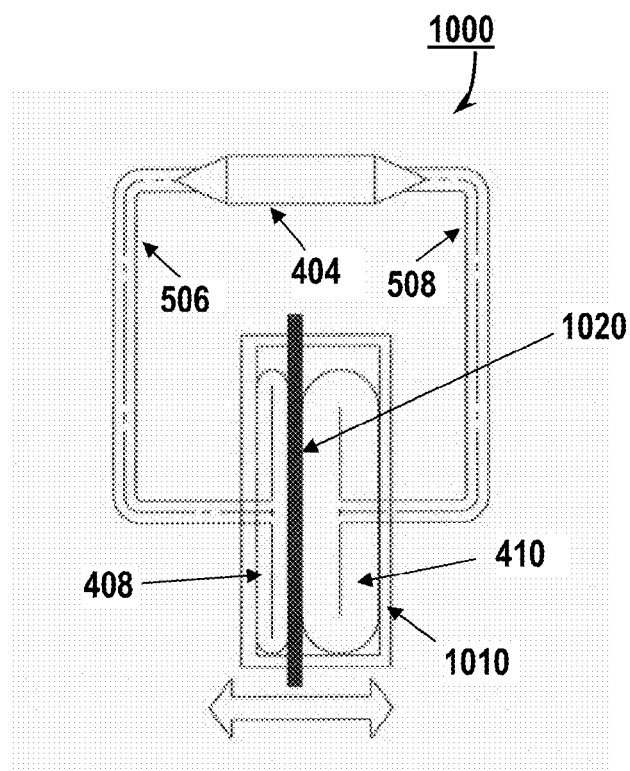
FIG. 10 is a schematic illustration of another bioreactor apparatus in accordance with even further embodiments of the present disclosure.

Another exemplary hollow-tube bioreactor system 1000 in accordance with yet further exemplary embodiments of the present disclosure is shown in FIG. 10. The bioreactor system 1000 includes a chamber 404 that contains a plurality of hollow fibers 510 (not shown), as described above. Opposite ends of the fiber lumens are in fluid communication with tubes 506, 508, as described above. The interior volume of a first reservoir 408 is coupled to the tube 506, and the interior volume of a second reservoir 410 is coupled to the tube 508. The reservoirs are formed at least partially of a deformable material, e.g. as described above, and contain cell-culture media 104 and/or gas 402 (not shown). The reservoirs 408, 410 are provided in a rigid enclosure 1010 as shown in FIG. 10. A plate 1020 is provided within the rigid enclosure 1010, between the reservoirs 408, 410. Appropriate valves, caps, or the like (not shown) can also be provided, e.g., in the walls of the reservoirs 408, 410 with access from the exterior of enclosure 1010 to facilitate access to the contents of the reservoirs 408, 410 as described above.

The plate 1020 can be configured to be translated back and forth within the enclosure 1010 as indicated by the hollow arrow in FIG. 10, e.g., using a conventional translating arrangement. As the plate is moved towards a reservoir, it compresses the reservoir against an inner wall of the enclosure 1010 and forces the fluids therein (e.g., media 104 and gas 402) to be controllably expelled from that reservoir, through the hollow fibers 510 in the chamber 404, and into the other reservoir via tubes 506 and 508. The plate 1020 can then be moved in the opposite direction. This cycle can be repeated to provide alternating flows of media 104 and gas 402 through the bioreactor. Other shapes and/or specific arrangements of the plate 1020 and enclosure 1010, which can be configured to operate in a similar manner to provide flows of media 104 and/or gas 402 through the bioreactor, can be used in further embodiments of the present disclosure.

Similar to the exemplary systems 800 and 900 shown in FIGS. 8 and 9, respectively, the order of expulsion of liquid media 104 and gas 402 from each of the reservoirs 408, 410 can be determined by where the tubes 506, 508 attach or couple to the reservoirs 408, 410. For example, the schematic diagram shown in FIG. 10 can be considered as a top-down view of the bioreactor system 1000, with gravity directed into the plane of the page. From this perspective, the tube coupling points may be at or near either the top or the bottom of the reservoirs 408, 410. Upper coupling point locations will lead to will lead to the gas 402 being expelled first from a reservoir, followed by the liquid media 104. Conversely, lower coupling point locations will lead to the liquid media 104 being forced from a reservoir before the gas 402 as the plate 1020 applies pressure to the reservoir. Either configuration may be used, e.g., based on particular needs and configuration of the overall system.

The various arrangements and methods for directing fluids through the bioreactor systems 700, 800, 900 and 1000 shown in FIGS. 7, 8, 9 and 10, respectively, can also be applied to conventional liquid-only hollow-fiber reactors. Thus, in addition to providing bioreactor systems that provide efficient oxygenation by flowing liquid media and gases through the fibers, certain embodiments of the present disclosure may further provide improved methods for inducing and controlling the flow of liquid media through conventional hollow-fiber bioreactor cartridges.

In a further exemplary embodiment, an exemplary gravity-driven bioreactor system 400, such as that illustrated in FIGS. 4-6, can be configured to provide tilting of the chamber 404 as flow of the media 104 and gas 402 is induced via gravitational forces. An exemplary configuration and procedure for such flow processes is shown schematically in FIGS. 11A-11D. The exemplary bioreactor system includes the chamber 404 containing the hollow fibers 510 (not shown), and reservoirs 408 and 410 provided in communication with the hollow fibers 510 within the chamber 404 via tubes 506 and 508, respectively, as described herein above. The chamber 404 is configured to be tiltable such that one end thereof can be higher than the other end, e.g., such that the longitudinal axis of the chamber 404 (which can be substantially parallel to the fibers 510) is at some angle relative to a horizontal orientation. For example, the chamber 404 can be affixed to a pivoting stand or support (not shown), held by a rotatable clamping arrangement, etc. The reservoirs 408, 410 can be movable relative to the chamber while being connected to it by tubes 506, 508.

Figure 11A:
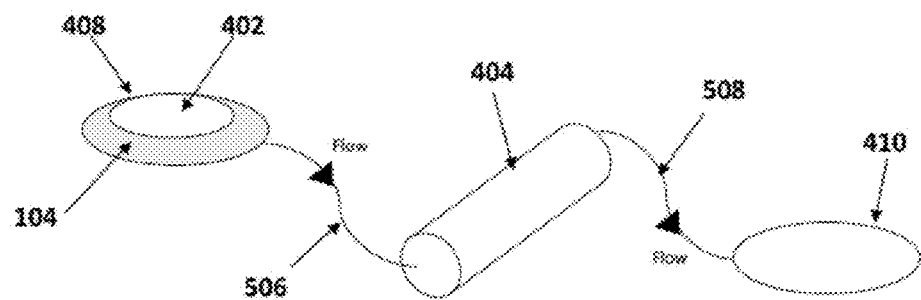
FIGS. 11A-11D illustrate an operational sequence for a gravity-driven bioreactor apparatus in accordance with further embodiments of the present disclosure.

As shown in FIG. 11A, the reservoir 408 can initially contain a quantity of the media 104 and gas 402. The chamber 404 can be tilted relative to a substantially horizontal position such that the end distal to reservoir 408 is elevated relative to the proximal end of chamber 404, as shown in FIG. 11A. The reservoir 408 can be positioned at an elevation higher than that of the distal end of chamber 404, as shown in FIG. 11A. In this exemplary configuration, liquid media 104 can flow through tube 506 and "uphill" through the hollow fibers 510 (not shown) within the chamber 404. The media 104 can then exit the distal end of the fibers 510 through tube 508 and into reservoir 410.

Figure 11B:
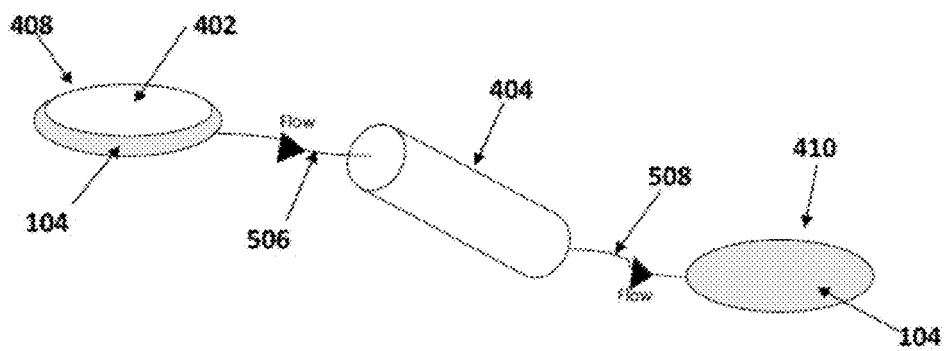
Figure 11C:
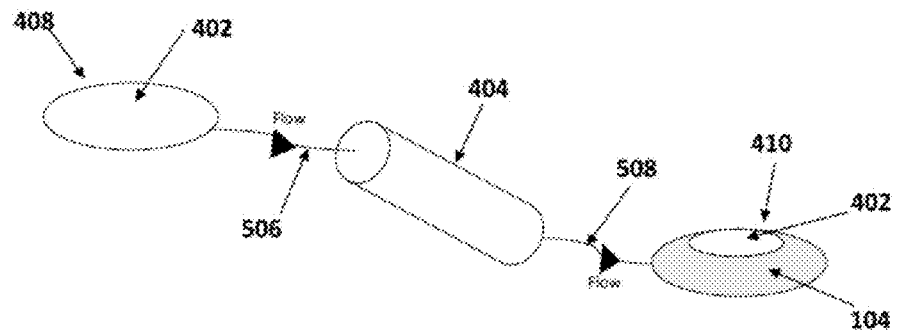

After some, most, or all of the liquid media 104 has flowed out of reservoir 408, the chamber 404 can be tilted in an opposite direction such that the proximal end thereof is higher than the distal end, as shown in FIG. 11B. In this next configuration, flow of the media 104 continues through the hollow fibers 510 and into the reservoir 410, but in a "downhill" direction. When most or all of the media 104 has flowed out of reservoir 408, some of the gas 402 initially provided in the reservoir 408 will be drawn through the hollow fibers 510 and then flow through tube 506 and into reservoir 410, as shown in FIG. 11C. Additional gas 402 can be flowed from reservoir 408 through the fibers 510, e.g., by squeezing or compressing the reservoir 408 (if it is made of a flexible/deformable material), by using a conventional pumping arrangement to propel further gas 402 out of reservoir 408 and through the fibers 510, etc. A conventional pumping arrangement, if present, can optionally be used to also propel the liquid media 104 through the fibers 510.

Figure 11D:
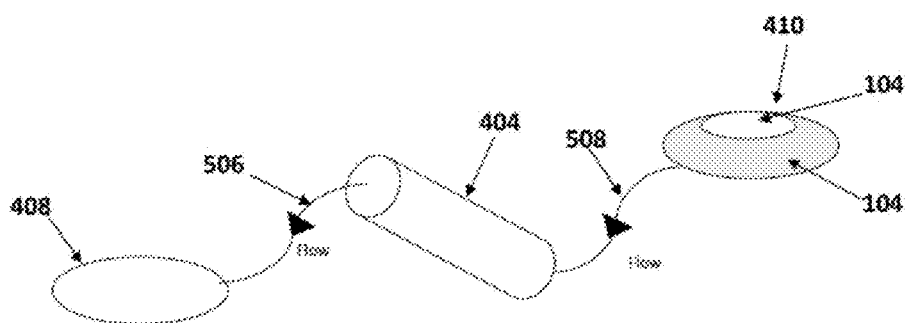

After a particular amount of liquid media 104 and gas 402 have flowed from reservoir 408, through the fibers 510 in the chamber 404, and into reservoir 410, the configuration can be reversed to generate flows through the fibers 510 in an opposite direction. For example, the process illustrated in FIGS. 11A-C can be reversed by elevating reservoir 410 relative to the raised end of chamber 404 and lowering reservoir 408, as shown in FIG. 11D. This exemplary configuration can generate sequential flow of the media 104 and gas 402 from reservoir 410 through tube 508, through the hollow fibers 510 in the opposite direction, and through tube 506 and into reservoir 408. In this manner, controlled, alternating flows of the media 104 and gas 402 through the hollow fibers 510 in the chamber 404 can be achieved, with some of the flow being in an "uphill" direction through the fibers 510 during each flow cycle.

Various features and options for the exemplary bioreactor system and procedure illustrated in FIGS. 11A-D can be similar to those described herein above with respect to other embodiments of the disclosure. For example, such system and procedure can include the various fluid pumping arrangements shown in FIGS. 7-10, and/or the various sensors, control systems, valves, ports, etc. described herein above with respect to other embodiments of the disclosure, any of which can be used with a tilted chamber 404.

Tilting the chamber 404 to generate an "uphill" flow for at least a portion of the liquid media 104 and/or gas 402 can provide several advantages. For example, when preparing a new hollow-fiber bioreactor such as those described herein for use, the fibers 510 should be conditioned to remove any residual materials accruing from the manufacturing process, which could impede transfer of media 104 or gas 402 through the fibers 510 and to ensure that proper surface condition exists on the outside of the fibers 510 to support cell adhesion. This conditioning can be achieved by thoroughly washing the fibers 510 with an appropriate cleaning solution and by pulling this solution out of the central lumens and through the fiber walls, e.g., by withdrawing it through the ports 520 that are in communication with the extra-capillary space 516 within the chamber 404. A chamber 404 that is oriented in a substantially horizontal direction may not support a complete filling of the uppermost fibers 510 within the chamber 404, which can result in an incomplete conditioning. By tilting the chamber 404 upward such that the flow is uphill, the fibers 510 can fill with the solution from the lower end up, thus completely filling all of the fibers 510 uniformly. Such tilting can also facilitate removal of any gases that may be present in the extra-capillary space 516 to create a media-filled volume to support the subsequent introduction of cells.

A further advantage of tilting the chamber 404 during operation can arise from the resultant gravity-induced partial pressure change in the extra-capillary space 516 that contains the cells being cultivated. The lower end of the media-filled extra-capillary space 516 of the chamber and the partially-filled central lumens of the hollow fibers 510 will have an elevated local pressure because of the hydrostatic head. The extra-capillary space 516 at the elevated or raised end of the chamber 404 can have a lower local pressure environment, which may tend to draw more gases from the lumen of the gas-filled fibers 510 through the fiber walls.

Further, as liquid media 104 begins to flow into the fibers 510 at the lowered end of the chamber 404, as shown in FIG. 11A, any trapped gas bubbles may be pushed through the central lumens of the fibers 510, which can force residual media 104 in the fibers 510 out of the elevated end. This process can increase the local pressure of the gas and media mixture within the fiber lumens, thereby increasing the rate of transfer through the fiber walls and into the extra-capillary space 516. As pressurized gas 402 exits through the elevated ends of the fibers 510 and further liquid media 104 enters the fiber lumens at the lowered end, the fibers 510 can uniformly fill with flowing media 104. As the media 104 continues to flow, internal flow resistance in the fiber lumens may create a higher pressure within the lumens relative to the pressure in the extra-capillary space 516, which can promote an enhanced flow of media 104 from the lumens into the lower region of the extra-capillary space 516.

When the media 104 has reached equilibrium with the fluid level in the feed line 506, such that this fluid level approximately corresponds to the height of the upper end of the chamber 404, further flow may substantially stop and the pressure within the extra-capillary space 516 can attain a static profile. At this point, the chamber 404 can be tilted in the opposite direction, as shown in FIG. 11B. The liquid media 104 remaining in the reservoir 408 and tube 506 can then flow "downhill" through the fibers 510, and a capillary effect may retain a residual amount of such media 104 in the fibers 510. After the chamber 404 is tilted in the opposite direction, the extra-capillary space 516 area can exhibit a reversed profile of partial and hydrostatic pressures. Gas 402 from the reservoir 408 that then flows through the fibers 510 as the liquid media 402 exits the lower end can now be preferentially drawn into the extra-capillary space 516 area at the upper end of the chamber, as shown in FIG. 11C, because of the lowered hydrostatic pressure in the extra-capillary space 516 at this upper end of the chamber 404. The durations of these flow and tilting processes can be controlled to improve or optimize the environment of the cultured cells in the extra-capillary space 516, e.g., using predetermined parameters, signals provided by one or more sensors as described herein above, etc.

By reversing the flow of media 104, tilting the chamber 404, and introducing a gas exchange enhanced by such tilting that also reverses with the media flow, gradients that could form over time within the environment of the extra-capillary space 516 can be greatly reduced, thereby maintaining a more uniform cell growth environment. Accordingly, higher-capacity bioreactors having larger fiber surface areas can be designed that include more fibers 510 rather than longer fibers 510, which can help to maintain uniformity of conditions in the extra-capillary space 516 over time.

Figure 12:
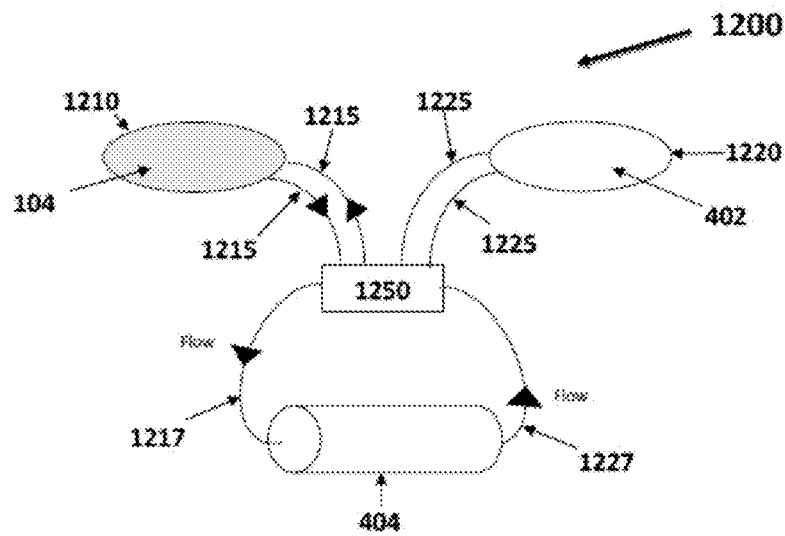
FIG. 12 is a schematic illustration of another bioreactor apparatus in accordance with further embodiments of the present disclosure.

A further embodiment of an exemplary fiber-based bioreactor system 1200 is shown in FIG. 12. The bioreactor 1200 includes a chamber 404 that contains a plurality of permeable fibers 510 therein (not shown) that can be secured at or near their ends by potting structures 512, 514 (not shown), which can further provide an extra-capillary space 516 outside of the fibers 510 and within the chamber 404, similar to the embodiments described herein above and shown in FIGS. 4 and 5. The bioreactor 1200 further includes separate reservoirs 1210, 1220 that contain liquid media 104 and gas 402, respectively. The reservoirs 1210, 1220 are in fluid communication with a pump arrangement 1250 via supply conduits 1215 and 1225, respectively. The pump arrangement 1250 is also in fluid communication with opposite ends of the fiber lumens in the chamber 404 via delivery conduits 1217 and 1227.

The pump arrangement 1250 can include one or more valve arrangements configurable to direct flows of liquid media 104 and gas 402 from the reservoirs 1210, 1220, through the delivery conduits 1217, 1227, through the lumens of the fibers 510, and back to the reservoirs 1210, 1220. The pump arrangement 1250 can be configured such that first reservoirs 1210, 1220 can be separately directed to be in fluid communication with fiber lumens at a first end of the chamber 404, and second reservoirs 1210, 1220 can be separately directed to be in fluid communication with fiber lumens at a second end of the chamber 404.

For example, in a first process, the pump arrangement 1250 can be configured to flow liquid media 104 from reservoir 1210 through a first supply conduit 1215 and through delivery conduit 1217 into the fibers 510, as shown in FIG. 12. Media 104 exiting the opposite end of the fibers 510 can be pumped back to the pump arrangement 1250 via delivery conduit 1227 and back into the reservoir 1210 through a second supply conduit 1215. The pump arrangement can also be configured to reverse the flow directions, such that liquid media 104 flows into the fibers 510 through delivery conduit 1227, and back to the pump arrangement 1250 and reservoir 1210 through delivery conduit 1217.

In an analogous manner, the pump arrangement 1250 can be capable of directing a flow of gas 402 from reservoir 1220 through a first supply conduit 1225 and delivery conduit 1217 into the fibers 510, and to pump such gas 402 back to the reservoir 1220 via delivery conduit 1227 and a second supply conduit 1225. The pump arrangement 1250 can also be capable of reversing this flow path of gas 402 through the various conduits and fiber lumens.

The pump arrangement 1250 can include conventional valve arrangements, connectors, ducts and the like, such that the flow of media 104 and gas 402 can be controllably directed through the various conduits and lumens as described above. In this manner, the bioreactor system 1200 can provide sequential or alternating flows of media 104 and gas 402 through the fibers 510 in the chamber 404, and such flow directions can be reversed if desired, which can help to maintain a homogenous conditions along the length of the extra-capillary space 516 within the chamber 404. The chamber 404 can optionally be configured to be tilted during operation of the bioreactor 1200, e.g., as shown in FIGS. 11A-D.

Figure 13:
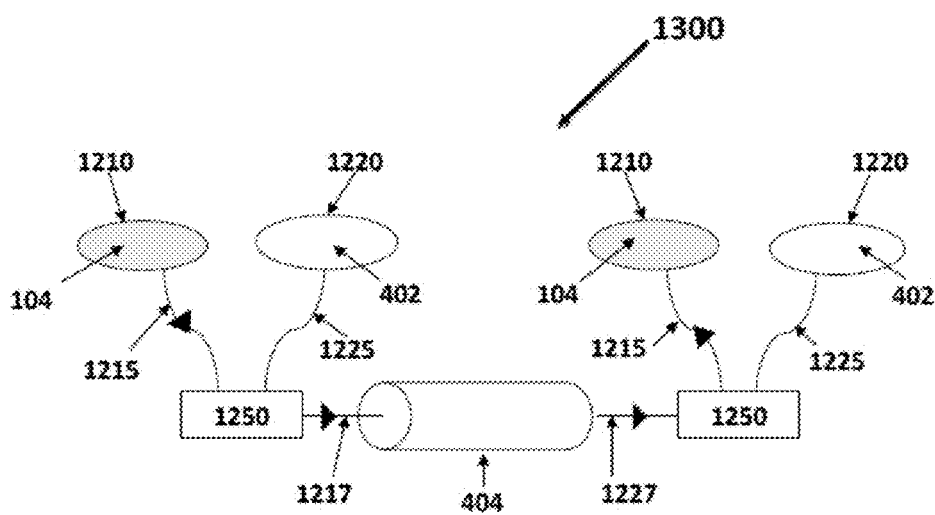
FIG. 13 is a schematic illustration of still another bioreactor apparatus in accordance with further embodiments of the present disclosure.

In a further exemplary embodiment, a fiber-based bioreactor system 1300 that is capable of providing both liquid and gas flows through lumens in the permeable fibers is shown in FIG. 13. The bioreactor system 1300 includes a chamber 404 that contains a plurality of permeable fibers 510 therein (not shown) that can be secured at or near their ends by potting structures 512, 514 (not shown), which can further provide an extra-capillary space 516 outside of the fibers 510 and within the chamber 404, similar to the embodiments described herein above and shown in FIGS. 4 and 5. The bioreactor system 1300 further includes two pump arrangements 1250, where the pump arrangements 1250 are provided in fluid communication with opposite ends of the hollow fibers 510 within the chamber 404 via delivery conduits 1217 and 1227. Reservoirs 1210, 1220 that contain liquid media 104 and gas 402, respectively, can be provided in communication with each pump arrangement 1250 through supply conduits 1215 and 1225, respectively. Each pump arrangement 1250 can include a valve arrangement in communication with supply conduits 1215 and 1225 as shown in FIG. 13, where the valve arrangement is configured to be capable of directing flow between either liquid reservoir 1210 or gas reservoir 1220 and the fibers 510 within the chamber 404.

In an exemplary procedure, the bioreactor system 1300 can be operated such that the valve arrangements 1310 provide a pathway between the two liquid reservoirs 1210, with the gas reservoirs 1220 being shut off from the flow path, as shown in FIG. 13. One or both pump arrangements 1250 can be activated to flow liquid media 104 through the fibers 510 from one reservoir 1210 to the opposite reservoir 1210. This flow direction can be reversed periodically if desired. The valve arrangements 1310 can then be operated to provide a pathway between the two gas reservoirs 1220, with the liquid reservoirs 1210 being shut off from the flow path. One or both pump arrangements 1250 can then be activated to flow gas 402 through the fibers 510 in the chamber 404, from one reservoir 1220 to the opposite reservoir 1220. This flow direction for the gas 402 can also be reversed periodically if desired. The chamber 404 can optionally be configured to be tilted during operation of the bioreactor 1300, e.g., as shown in FIGS. 11A-D.

In certain embodiments, one of the pump arrangements 1250 shown in FIG. 13 can be omitted, and a single pump arrangement 1250 can be operated to push liquid media 104 and gas 402 from one pair of reservoirs 1210, 1220 through the hollow fibers 510 and into the opposite reservoirs 1210, 1220, and then to pull liquid media 104 and gas 402 from this opposite pair of reservoirs 1210, 1220 through the fibers 510 and into the proximal reservoirs 1210, 1220. In further embodiments, each pump arrangement 1250 can be connected to a single reservoir that contains both liquid media 104 and gas 402. Operation of the pump arrangement 1250 can be performed such that flow of the liquid media 104 through the fibers 510 is followed by flow of gas 402 therethrough, as described herein above.

While various embodiments of the present disclosure have been described above, it should be understood that they have been presented by way of example, and not limitation. It will be apparent to persons skilled in the relevant art that various changes in form and detail can be made therein without departing from the spirit and scope of the disclosure. Thus the present disclosure should not be limited by any of the above-described exemplary embodiments, but should be defined only in accordance with the following claims and their equivalents. Although the disclosure provides descriptions of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

It will thus be appreciated that those skilled in the art will be able to devise numerous systems, arrangements and methods which, although not explicitly shown or described herein, embody the principles of the disclosure and are thus within the spirit and scope of the present disclosure. In addition, all publications, patents and patent applications referenced herein are incorporated herein by reference in their entireties.

What is claimed is:

1. A method for growing cells using an apparatus having at least two reservoirs, an enclosed chamber, and at least one hollow fiber, wherein the at least one hollow fiber is disposed within the enclosed chamber such that an extra-capillary space is defined between an interior of the enclosed chamber and an exterior surface of the at least one hollow fiber, and the at least one hollow fiber has a lumen passing therethrough, the method comprising:
   placing cells into the extra-capillary space;
   providing the liquid media in at least one of the at least two reservoirs;
   providing the gas in at least one of the at least two reservoirs; and
   generating alternating directed flows of the liquid media and of the gas through the lumen of the at least one hollow fiber,
   whereby the liquid media and the gas are capable of providing nutrients and/or oxygen through walls of the at least one hollow fiber to nourish the cells in the extra-capillary space.

2. The method of claim 1, wherein the alternating directed flows of the liquid media and of the gas comprise a first directed flow of the liquid media through the lumen of the at least one hollow fiber in a first direction and a second directed flow of the gas in the same first direction through the lumen of the at least one hollow fiber.

3. The method of claim 2, wherein the alternating directed flows of the liquid media and of the gas comprise a third directed flow of the liquid media through the lumen of the at least one hollow fiber in a direction opposite to that of the first directed flow.

4. The method of claim 3, wherein the alternating directed flows of the liquid media and of the gas comprise a fourth directed flow of the gas through the lumen of the at least one hollow fiber in a direction opposite to that of the second directed flow.

5. The method of claim 1, wherein the alternating directed flows are generated by gravitational forces.

6. The method of claim 1, wherein each of the at least two reservoirs are at least partially deformable, and wherein the alternating directed flows are generated by applying a force to at least one reservoir.

7. The method of claim 6, wherein the force is applied using a roller arrangement.

8. The method of claim 1, wherein the alternating directed flows are generated using a piston arrangement.

9. The method of claim 1, wherein the alternating directed flows are generated using at least one pump arrangement.

10. The method of claim 1, further comprising tilting the chamber such that at least one of the directed flow of the liquid media and the directed flow of the gas through the lumen of the at least one hollow fiber is uphill.

11. The method of claim 1, further comprising providing the liquid media in a reservoir that contains substantially no gas, and providing the gas in a further reservoir that contains substantially no liquid media.

12. The method of claim 1, wherein the alternating directed flows are generated using at least one valve arrangement.

13. The method of claim 1, wherein the alternating directed flows of the liquid media and of the gas comprise a first directed flow of the liquid media through the lumen of the at least one hollow fiber in a first direction and a second directed flow of the gas through the lumen of the at least one hollow fiber in a direction opposite to the first direction.

* * * * *